United States Patent
Hayashi et al.

(10) Patent No.: US 9,717,462 B2
(45) Date of Patent: Aug. 1, 2017

(54) BIOLOGICAL INFORMATION MEASUREMENT METHOD AND APPARATUS WITH VARIABLE LOOP FILTER

(71) Applicant: Murata Manufacturing Co., Ltd., Nagaokakyo-shi, Kyoto-fu (JP)

(72) Inventors: Takanori Hayashi, Nagaokakyo (JP); Yasushi Sato, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 15/077,062

(22) Filed: Mar. 22, 2016

(65) Prior Publication Data

US 2016/0199005 A1    Jul. 14, 2016

Related U.S. Application Data

(63) Continuation of application No. PCT/JP2014/074372, filed on Sep. 16, 2014.

(30) Foreign Application Priority Data

Sep. 26, 2013 (JP) ................................ 2013-199745

(51) Int. Cl.
*A61B 5/0428* (2006.01)
*A61B 5/00* (2006.01)
(Continued)

(52) U.S. Cl.
CPC .......... *A61B 5/721* (2013.01); *A61B 5/02416* (2013.01); *A61B 5/02427* (2013.01);
(Continued)

(58) Field of Classification Search
None
See application file for complete search history.

(56) References Cited

U.S. PATENT DOCUMENTS 4,156,855 A   5/1979  Crowley
RE31,097 E * 12/1982 Vas .......................... A61B 5/11
                                                                600/500

(Continued)

FOREIGN PATENT DOCUMENTS

| JP | 10-248819 A | 9/1998 |
| JP | H10-285021 A | 10/1998 |
| JP | 2003028952 A | 1/2003 |
| JP | 2007-105133 A | 4/2007 |

(Continued)

OTHER PUBLICATIONS

International Search Report for PCT/JP2014/074372 date of mailing Dec. 22, 2014.
Written Opinion for PCT/JP2014/074372 date of mailing Dec. 22, 2014.

*Primary Examiner* — Kennedy Schaetzle
(74) *Attorney, Agent, or Firm* — Arent Fox LLP

(57) ABSTRACT

A biological information measurement apparatus includes a phase/frequency comparison unit that outputs a deviation signal based on a phase difference between a biological signal and an oscillation signal; a variable loop filter that varies a cutoff frequency and a phase margin and that selectively blocks a signal of a predetermined frequency band contained in the deviation signal; and a voltage controlled oscillation unit that generates the oscillation signal in accordance with the deviation signal that has passed through the variable loop filter. The apparatus further includes a CPU that estimates a SN ratio of the biological signal and analyzes a phase difference/frequency difference between the biological signal outputted from the comparison unit and the oscillation signal. The CPU further changes a constant of the variable loop filter based on the SN ratio and the phase difference/frequency difference.

20 Claims, 7 Drawing Sheets

(51) Int. Cl.
*A61B 5/024* (2006.01)
*H03L 7/093* (2006.01)
*H03L 7/107* (2006.01)
*A61B 5/0245* (2006.01)
*A61B 5/0452* (2006.01)
*A61B 5/0456* (2006.01)

(52) U.S. Cl.
CPC ............ *A61B 5/725* (2013.01); *A61B 5/7207* (2013.01); *A61B 5/7225* (2013.01); *A61B 5/7246* (2013.01); *H03L 7/093* (2013.01); *H03L 7/107* (2013.01); *A61B 5/0245* (2013.01); *A61B 5/0452* (2013.01); *A61B 5/0456* (2013.01)

(56) References Cited

U.S. PATENT DOCUMENTS

| | | | |
|---|---|---|---|
| 7,385,443 B1* | 6/2008 | Denison | H03F 3/38 330/10 |
| 9,351,653 B1* | 5/2016 | Harrison | A61B 5/04014 |
| 2006/0173364 A1* | 8/2006 | Clancy | A61B 5/04 600/485 |
| 2011/0227571 A1 | 9/2011 | Sekiguchi et al. | |

FOREIGN PATENT DOCUMENTS

| | | |
|---|---|---|
| JP | 2007-251571 A | 9/2007 |
| JP | 2011-189079 A | 9/2011 |

* cited by examiner

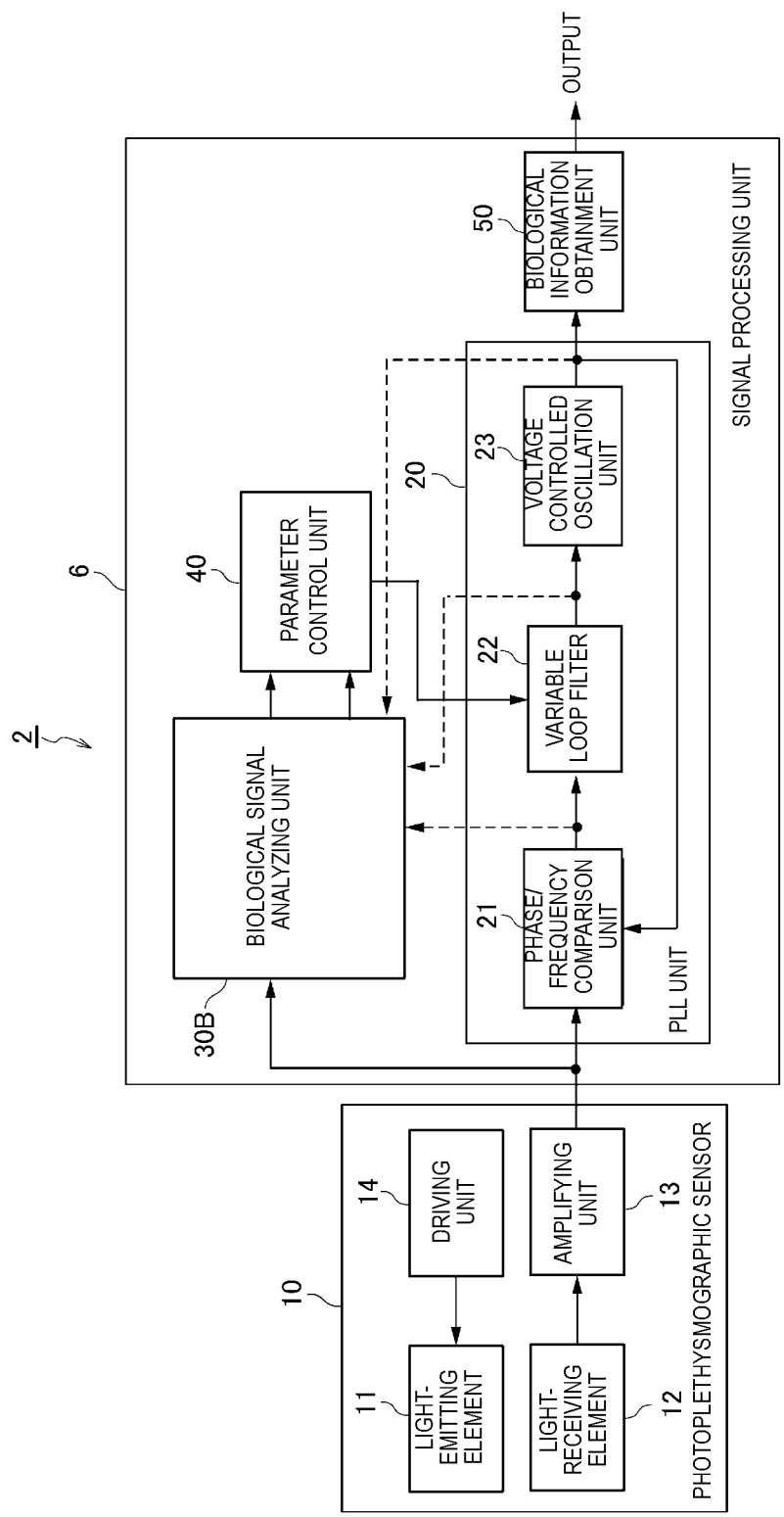

BIOLOGICAL INFORMATION MEASUREMENT METHOD AND APPARATUS WITH VARIABLE LOOP FILTER

CROSS REFERENCE TO RELATED APPLICATIONS

The present application is a continuation of PCT/JP2014/074372 filed Sep. 16, 2014, which claims priority to Japanese Patent Application No. 2013-199745, filed Sep. 26, 2013, the entire contents of each of which are incorporated herein by reference.

FIELD OF THE INVENTION

The present invention relates to biological information measurement apparatuses, and particularly relates to biological information measurement apparatuses that have phase synchronization circuits.

BACKGROUND

Phase synchronization circuits that output an oscillation signal whose phase is synchronized with an input signal (also called "PLLs", or "phase locked loops", hereinafter) have for some time been widely used in applications such as suppressing jitter in input signals of communication apparatuses and the like, clock frequency crossover, and so on. Phase synchronization circuits are also applied in apparatuses that measure biological information, such as heart rate, pulse rate, or the like (see Patent Document 1, for example). A light-receiving device described in Patent Document 1 converts a pulse wave signal contained in an optical signal detected by a light-receiving element into a digital signal using a hysteresis comparator, and measures a pulse beat interval by measuring an interval of pulses in the digital signal with a timer that uses a phase synchronization circuit.

With a phase synchronization circuit, it is preferable that the cutoff frequency of a loop filter be set while taking jitter, noise, and so on contained in the input signal into consideration so as to stabilize the output of the oscillation signal. Here, Patent Document 2 discloses a phase synchronization circuit that appropriately changes the cutoff frequency of a loop filter in accordance with jitter in an input signal. Specifically, in addition to a first phase synchronization circuit including a first phase comparator, a first loop filter, and a first oscillation circuit, this phase synchronization circuit further includes a PLL circuit that generates a reference signal whose phase is synchronized with the input signal and that has less phase noise than the input signal, a second phase comparator that detects a phase difference between the input signal and the reference signal, a low pass filter that integrates that output, and a filter control unit that controls the cutoff frequency of the first loop filter on the basis of a frequency component obtained by analyzing the frequency of that output. The cutoff frequency of the first loop filter is changed as appropriate in accordance with jitter in the input signal.

Patent Document 1: Japanese Unexamined Patent Application Publication No. 2007-105133.

Patent Document 2: Japanese Unexamined Patent Application Publication No. 2007-251571.

Incidentally, because pulse rates vary over time, biological signals such as electrocardiographs, photoplethysmographs, and so on experience a wider range of frequency fluctuation than the jitter in an input signal of a communication apparatus or the like, and are also more susceptible to artifacts (noise) superimposed on the signal due to body movements or the like.

Here, in the case where the phase synchronization circuit disclosed in Patent Document 2 is applied in an apparatus that measures biological information, an output signal that is less affected by jitter can be obtained by comparing the phases of the output of the PLL circuit, which has little phase noise, with the input signal (biological signal) in order to extract only a jitter component, and then controlling the cutoff frequency of the loop filter in accordance with the amount of jitter. However, according to this phase synchronization circuit, fluctuations in the output of the phase comparator caused by fluctuations in the base frequency of the biological signal cannot be distinguished from fluctuations in the output of the phase comparator caused by fluctuations in artifacts such as jitter. Therefore, even if there is no jitter in the biological signal, when the base frequency of the biological signal fluctuates suddenly, the cutoff frequency of the loop filter is controlled in the same manner as if there was superimposed jitter, which can greatly worsen the lock-up time of the PLL.

SUMMARY OF THE INVENTION

Having been achieved in order to solve the stated problem, it is an object of the present invention to provide, in a biological information measurement apparatus having a phase synchronization circuit, a biological information measurement apparatus capable of achieving a high level of both robustness with respect to artifacts and a reduction in lock-up time.

A biological information measurement apparatus according to the present invention includes a biological signal detecting unit or sensor that detects a biological signal; a phase/frequency comparator that outputs a deviation signal based on a phase difference/frequency difference between the biological signal detected by the biological signal detecting unit and an oscillation signal; a variable loop filter unit whose cutoff frequency and/or phase margin can be varied, and that selectively blocks a signal in a predetermined frequency band contained in the deviation signal outputted by the phase/frequency comparator; a voltage controlled oscillator that generates and outputs an oscillation signal in accordance with the deviation signal that has passed through the variable loop filter unit; a biological signal analyzing unit that analyzes a phase, a frequency, and a SN ratio of the biological signal; and a parameter control unit that changes a constant of the variable loop filter unit on the basis of an analysis result obtained by the biological signal analyzing unit.

According to the biological information measurement apparatus of the present invention, the phase, frequency, and SN ratio of the biological signal are analyzed, and the constant of the variable loop filter unit is changed in accordance with that analysis result. As such, a PLL can be synchronized appropriately in accordance with fluctuations in the frequency of the inputted biological signal, a state of artifacts, and so on. As a result, an output signal that is not susceptible to the influence of artifacts can be obtained in the case where artifacts are superimposed on the biological signal, and PLL lock-up time can be reduced in the case where no artifacts are superimposed. Accordingly, robustness with respect to artifacts and a reduction in lock-up time can both be achieved at a high level in a biological information measurement apparatus having a phase synchronization circuit.

In the biological information measurement apparatus according to the present invention, it is preferable that the biological signal analyzing unit analyze the phase, the frequency, and the SN ratio of the biological signal by carrying out an orthogonal transform on the biological signal.

According to this configuration, the phase, frequency, and SN ratio of the biological signal, in which the pulse rate varies over time and which is easily susceptible to superimposed artifacts caused by body movements and the like, can be analyzed appropriately.

In the biological information measurement apparatus according to the present invention, it is preferable that the biological signal analyzing unit include an SN analyzing unit that estimates the SN ratio of the biological signal by carrying out an autocorrelation analysis on the biological signal, and a phase/frequency analyzing unit that analyzes the phase difference/frequency difference between the biological signal and the oscillation signal on the basis of the output of the phase/frequency comparator; and that the parameter control unit change the constant of the variable loop filter unit based on the SN ratio estimated by the SN analyzing unit and the phase difference/frequency difference analyzed by the phase/frequency analyzing unit.

In this case, the constant of the variable loop filter unit is changed in accordance with the analysis result from the SN analyzing unit (the SN ratio) and the analysis result from the phase/frequency analyzing unit (the phase difference/frequency difference). As such, the PLL can be synchronized more appropriately in accordance with fluctuations in the frequency of the inputted biological signal, a state of artifacts, and so on. As a result, an output signal that is not susceptible to the influence of artifacts can be obtained in the case where artifacts are superimposed on the biological signal due to body movements or the like, and PLL lock-up time can be reduced in the case where no artifacts are superimposed. Accordingly, robustness with respect to artifacts and a reduction in lock-up time can both be achieved at an even higher level.

In the biological information measurement apparatus according to the present invention, it is preferable that the parameter control unit adjust the phase margin of the variable loop filter unit by adjusting a phase range of a differential element of the variable loop filter unit.

Here, the phase margin increases when the phase range is reduced, and the phase margin decreases when the phase range is increased. That is, the phase margin, or in other words, convergence properties, can be adjusted by adjusting the phase range. In this case, by changing the phase range of the differential (D) element of the variable loop filter unit to adjust the phase margin, the convergence properties of the variable loop filter unit can be adjusted.

In the biological information measurement apparatus according to the present invention, it is preferable that the parameter control unit switch among a plurality of modes having different cutoff frequencies and phase margins on the basis of the SN ratio estimated by the SN analyzing unit and the phase difference/frequency difference analyzed by the phase/frequency analyzing unit.

In this case, the cutoff frequency and the phase margin can be changed by switching among the plurality of modes. As a result, an output signal that is not susceptible to the influence of artifacts can be obtained in the case where artifacts are superimposed on the biological signal, and PLL lock-up time can be reduced in the case where no artifacts are superimposed. Accordingly, both robustness with respect to artifacts and a reduction in lock-up time can be achieved at a high level.

In the biological information measurement apparatus according to the present invention, it is preferable, when switching among the plurality of modes, that the parameter control unit control the phase margin of the variable loop filter unit by adjusting a phase range of a differential element of the variable loop filter unit.

In this case, the phase range of the differential (D) element of the variable loop filter unit is adjusted when switching among the plurality of modes. Accordingly, the magnitude of the phase margin of the variable loop filter unit can be adjusted, and the convergence properties of the variable loop filter unit can be changed, by switching the mode.

In the biological information measurement apparatus according to the present invention, it is preferable that hysteresis be provided by the parameter control unit when switching among the plurality of modes. Doing so makes it possible to prevent erroneous operations (hunting) from occurring when switching modes.

In the biological information measurement apparatus according to the present invention, it is preferable that the plurality of modes include a noise mode, a following mode, and a normal mode; the noise mode be set so that the cutoff frequency is lower and the phase margin is higher than in the following mode; the following mode be set so that the cutoff frequency is higher and the phase margin is lower than in the noise mode; the normal mode be set so that the cutoff frequency and the phase margin are between those in the noise mode and those in the following mode; and the parameter control unit select the noise mode when the SN ratio is lower than a predetermined value, select the following mode when the SN ratio is higher than the predetermined value and the phase difference/frequency difference is higher than a predetermined threshold value, and select the normal mode when the SN ratio is higher than the predetermined value and the phase difference/frequency difference is lower than the predetermined threshold value.

In this case, artifacts caused by body movements or the like are determined to be superimposed on the biological signal in the case where the SN ratio is determined to be low, and the constant of the variable loop filter unit is switched to the noise mode, in which the cutoff frequency is low and the phase margin is high. On the other hand, in the case where the phase difference/frequency difference are determined to be high despite the SN ratio being high and it being determined that artifacts are not superimposed, it is determined that the PLL is not in synchronization with the biological signal on which artifacts are not superimposed, and the constant of the variable loop filter unit is switched to the following mode, in which the cutoff frequency is high and the phase margin is low. Meanwhile, in the case where the SN ratio is high and it is determined that artifacts are superimposed and that the phase difference/frequency difference is low, it is determined that the PLL is approximately in synchronization with the biological signal on which artifacts are not superimposed, and the constant of the variable loop filter unit is switched to the normal mode, which is located between the following mode and the noise mode. Accordingly, the cutoff frequency and the phase margin can be changed by switching among the stated three modes. As a result, robustness with respect to artifacts and a reduction in lock-up time can both be achieved at a high level.

According to the present invention, robustness with respect to artifacts and a reduction in lock-up time can both be achieved at a high level in a biological information measurement apparatus having a phase synchronization circuit.

BRIEF DESCRIPTION OF THE DRAWINGS

FIG. 7 is a block diagram illustrating the configuration of a biological information measurement apparatus according to a second embodiment.

DETAILED DESCRIPTION

Figure 1:
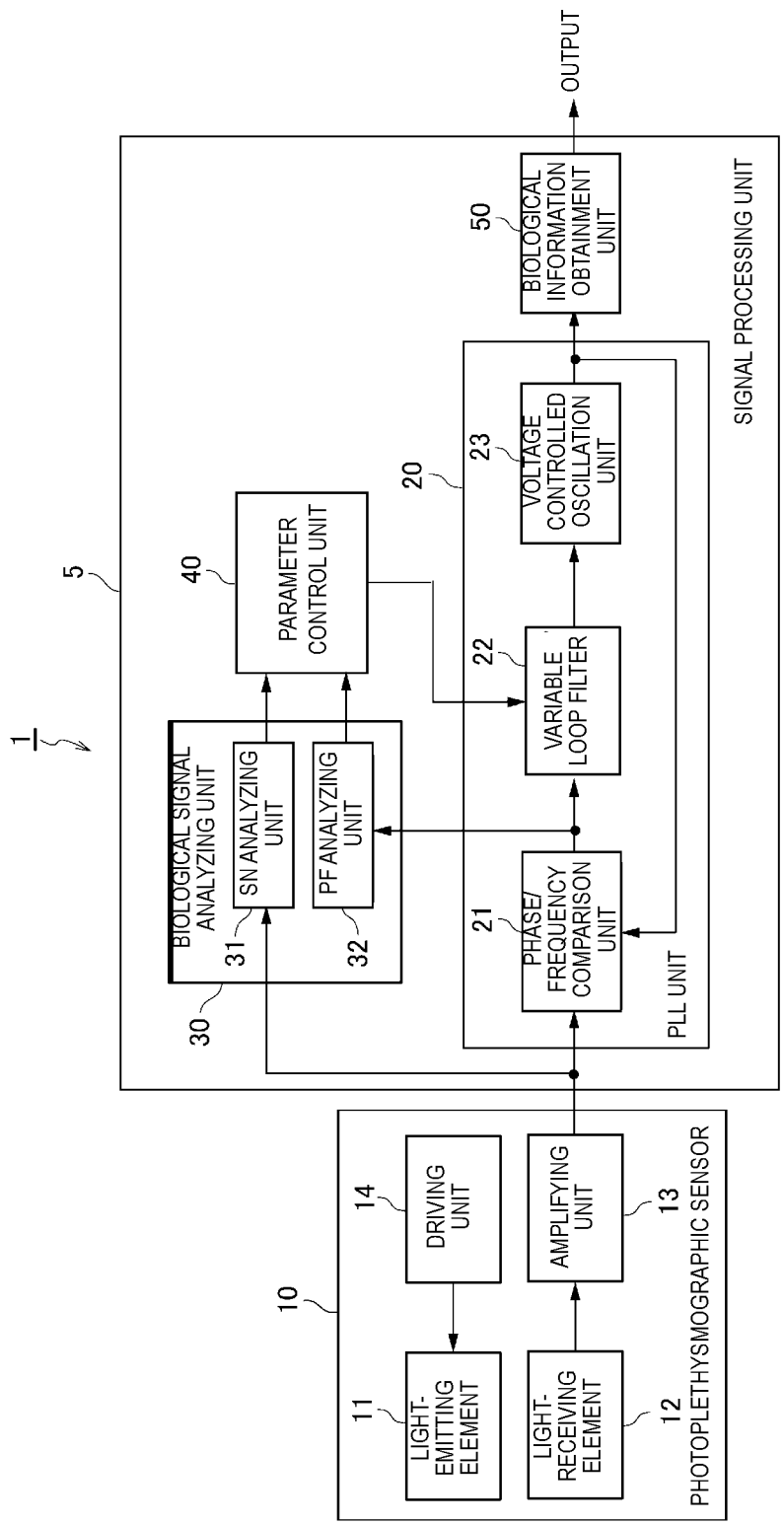
FIG. 1 is a block diagram illustrating the configuration of a biological information measurement apparatus according to a first embodiment.

Hereinafter, preferred embodiments of the present invention will be described in detail with reference to the drawings. In the drawings, the same reference numerals are used for identical or corresponding portions. Furthermore, in each of the drawings, the same reference numerals are appended to identical elements and redundant descriptions thereof will be omitted.

First Embodiment

Figure 2:
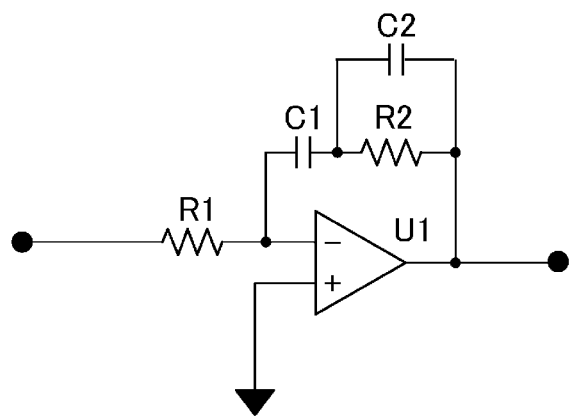
FIG. 2 is a circuit diagram illustrating an example of an analog filter (a variable loop filter) that constitutes the biological information measurement apparatus according to the first embodiment.
Figure 3:
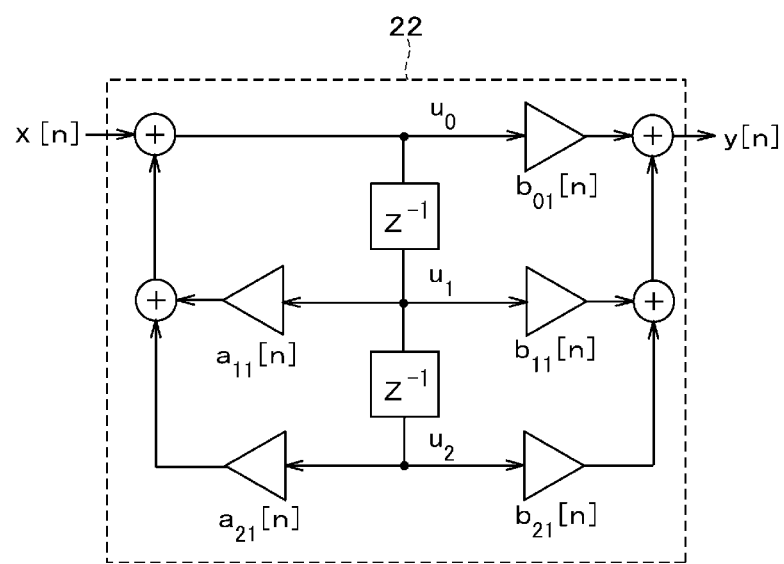
FIG. 3 is a diagram illustrating an example of a digital filter (a variable loop filter) obtained by converting the analog filter illustrated in FIG. 2.

First, the configuration of a biological information measurement apparatus 1 according to a first embodiment will be described using FIGS. 1 to 3. FIG. 1 is a block diagram illustrating the configuration of the biological information measurement apparatus 1. FIG. 2 is a circuit diagram illustrating an example of an analog filter (a variable loop filter 22) that constitutes the biological information measurement apparatus 1, and FIG. 3 is a diagram illustrating an example of a digital filter (the variable loop filter 22) obtained by converting the analog filter illustrated in FIG. 2. The present embodiment describes, as an example, a case where biological information such as a pulse rate is measured from a photoplethysmographic signal that serves as a biological signal. However, the biological signal is not limited to a photoplethysmographic signal, and an electrocardiac signal or the like may be employed instead, for example.

The biological information measurement apparatus 1 detects a photoplethysmographic signal and generates an oscillation signal whose phase is synchronized with the detected photoplethysmographic signal. Then, on the basis of the generated oscillation signal, the biological information measurement apparatus 1 measures biological information such as a pulse rate (a base frequency of the photoplethysmographic signal). To that end, the biological information measurement apparatus 1 includes a photoplethysmographic sensor 10 that generates the photoplethysmographic signal, and a signal processing unit 5 that generates an oscillation signal whose phase is synchronized with the photoplethysmographic signal and measures the biological information such as a pulse rate or the like. Various constituent elements will be described in detail hereinafter.

The photoplethysmographic sensor 10 is a sensor that uses light absorbance characteristics of bloodstream hemoglobin to optically detect the photoplethysmographic signal. The photoplethysmographic sensor 10 includes a light-emitting element 11, a light-receiving element 12, an amplifying unit 13, and a driving unit 14.

The light-emitting element 11 emits light in accordance with a pulse-form driving signal generated and outputted by the driving unit 14. For example, an LED, a VCSEL (Vertical Cavity Surface Emitting LASER), a resonant-type LED, or the like can be used as the light-emitting element 11.

The light-receiving element 12 outputs a detection signal based on the intensity of incident light that has been emitted from the light-emitting element 11 and then passed through a human body such as a fingertip or reflected by the human body. For example, a photodiode, a phototransistor, or the like can be effectively used as the light-receiving element 12. Note that a photodiode is used as the light-receiving element 12 in the present embodiment. The light-receiving element 12 is connected to the amplifying unit 13, and the detection signal (photoplethysmographic signal) obtained by the light-receiving element 12 is outputted to the amplifying unit 13.

The amplifying unit 13 is constituted by an amplifier using an op-amp or the like, for example, and amplifies the photoplethysmographic signal detected by the light-receiving element 12. The photoplethysmographic sensor 10 is connected to the signal processing unit 5, and the detected photoplethysmographic signal is outputted to the signal processing unit 5.

The signal processing unit 5 generates an oscillation signal whose phase is synchronized with the photoplethysmographic signal detected by the photoplethysmographic sensor 10, and measures biological information such as a pulse rate (a base frequency of the biological signal). To that end, the signal processing unit 5 includes a PLL unit 20, a biological signal analyzing unit 30, a parameter control unit 40, and a biological information obtainment unit 50. The PLL unit 20, meanwhile, includes a phase/frequency comparison unit (PFC) 21, the variable loop filter 22, and a voltage controlled oscillation unit (VCO) 23.

According to the exemplary embodiment, of the above-described units, the biological signal analyzing unit 30 (an SN analyzing unit 31 and a PF analyzing unit 32), the parameter control unit 40, the variable loop filter 22 (when constituted by a digital filter), and the biological information obtainment unit 50 can be functional units that are performed by a computer processing unit ("CPU") (or MCU) that carries out computational processes, a ROM that stores programs, data, and so on for causing that CPU to execute various processes, a RAM that temporarily stores various types of data such as processing results, and the like. In other words, the functions of the various above-described elements are realized by programs stored in the ROM being executed by the CPU. The present disclosure refers to each specific unit performing its associated algorithm, but it should be appreciated that such algorithms can be performed by the CPU according to the exemplary embodiment.

The PLL unit 20 compares the photoplethysmographic signal (an input signal) with the oscillation signal of the voltage controlled oscillation unit 23 (an output signal) using a phase/frequency comparison unit 21, and outputs a signal (a deviation signal) based on the magnitudes of a phase difference and a frequency difference. The deviation signal is then integrated using the variable loop filter 22 and inputted into the voltage controlled oscillation unit 23, thus generating (oscillating) the oscillation signal so as to eliminate the phase difference and the frequency difference between the oscillation signal of the voltage controlled oscillation unit 23 and the photoplethysmographic signal. The PLL unit 20 outputs a signal synchronized with the photoplethysmographic signal as a result of this series of operations.

As described above, the phase/frequency comparison unit 21 (i.e., a phase/frequency comparator) outputs a deviation signal based on the phase difference and the frequency difference between the obtained photoplethysmographic signal and the oscillation signal (a feedback signal) generated and outputted by the voltage controlled oscillation unit 23. To be more specific, when the difference between the photoplethysmographic signal and the oscillation signal is within one period, the phase/frequency comparison unit 21 compares the phases and outputs, as the deviation signal, a square wave of a positive or negative voltage with a duty ratio proportional to the phase difference. Meanwhile, when the difference between the photoplethysmographic signal and the oscillation signal exceeds one period, the phase/frequency comparison unit 21 functions as a frequency comparator, and outputs, as the deviation signal, a square wave of a positive or negative voltage with a duty ratio proportional to the frequency difference.

Note that a digital phase/frequency comparator, a voltage output phase/frequency comparator including a charge pumping circuit, or the like, for example, can be used as the phase/frequency comparison unit 21. The phase/frequency comparison unit 21 is connected to the variable loop filter 22 and the biological signal analyzing unit 30 (the PF analyzing unit 32), and the deviation signal indicating the phase difference and frequency difference between the photoplethysmographic signal and the oscillation signal is outputted to the variable loop filter 22 and the biological signal analyzing unit 30 (the PF analyzing unit 32).

The variable loop filter 22 can change a cutoff frequency at which the throughput of a signal is selectively stopped, and is a low pass filter that selectively blocks only signals of a predetermined frequency band contained in the deviation signal outputted by the phase/frequency comparison unit 21. By blocking unnecessary short-period fluctuations, the variable loop filter 22 suppresses needless oscillations that can arise due to short-period signal fluctuations being amplified in a circuit containing feedback. Note that the variable loop filter 22 is configured so that constants thereof (a cutoff frequency and a phase margin) can be changed by the parameter control unit 40, which will be described later.

An analog filter employing an operational amplifier (op-amp) and whose differential element can be changed, as illustrated in FIG. 2, can be used as the variable loop filter 22. Meanwhile, a second-order IIR (infinite impulse response) filter (a digital filter) or the like constituted by four adders, two delay elements, and five multipliers, such as that illustrated in FIG. 3, may be used as the variable loop filter 22. In this case, the constants of the respective elements are changed by changing the parameters (filter coefficients) of the multipliers. This will be described in detail later. The variable loop filter 22 is connected to the voltage controlled oscillation unit 23, and the variable loop filter 22 outputs the output signal (output voltage) to the voltage controlled oscillation unit 23.

The voltage controlled oscillation unit 23 (i.e., a voltage controlled oscillator) generates and outputs an oscillation signal having a frequency based on the output voltage from the variable loop filter 22 (that is, based on the filtered deviation signal). A voltage controlled oscillator such as a Colpitts VCO (voltage controlled oscillator), a voltage controlled quartz oscillator, or the like can be used as the voltage controlled oscillation unit 23, for example. Note that the above-described voltage controlled oscillation unit 23 may be realized through digital signal processing. The voltage controlled oscillation unit 23 may be configured to be used in combination with a frequency divider. Note that the voltage controlled oscillation unit 23 is connected to the phase/frequency comparison unit 21 and the biological information obtainment unit 50, and the oscillation signal generated by the voltage controlled oscillation unit 23 is outputted to the phase/frequency comparison unit 21 and the biological information obtainment unit 50.

The biological signal analyzing unit 30 analyzes the approximate frequency, phase, and SN ratio of the photoplethysmographic signal on the basis of the photoplethysmographic signal inputted from the photoplethysmographic sensor 10 and the output of the phase/frequency comparison unit 21. To that end, the biological signal analyzing unit 30 includes the SN analyzing unit 31, which estimates the SN ratio of the photoplethysmographic signal through an autocorrelation analysis on the photoplethysmographic signal, and the phase/frequency analyzing unit (also called "PF analyzing unit" hereinafter) 32, which analyzes the phase difference/frequency difference between the photoplethysmographic signal and the oscillation signal on the basis of the output of the phase/frequency comparison unit 21.

The SN analyzing unit 31 estimates the SN ratio of the photoplethysmographic signal through an autocorrelation analysis on the inputted photoplethysmographic signal. Specifically, the photoplethysmographic signal is normally a periodic signal in which the same pattern repeats every set interval, and thus by normalizing a coefficient $r_k$ obtained through the autocorrelation function indicated in the following Formula (1) with $r_0$ and finding an integrated value thereof, the SN analyzing unit 31 analyzes the periodicity of the photoplethysmographic signal, whether or not artifacts are superimposed, and so on (μ in Formula (1) represents an average value of a photoplethysmographic signal x, and N represents the number of data in a range subject to the autocorrelation analysis).

Formula 1

$$r_k = \frac{1}{N}\sum_{n=0}^{N-1}(x[n]-\mu)\cdot(x[n+k]-\mu) \quad (k=0, 1, \ldots, N-1) \tag{1}$$

The PF analyzing unit 32 includes a fixed-constant reference low pass filter (LPF), and carries out its analysis by monitoring an output value (an amplitude value) of the reference LPF and changes therein (a differential value). Here, in the case where the output value (amplitude value) of the reference LPF and a change in that output value are lower than a predetermined threshold value, the PF analyzing unit 32 determines that the PLL unit 20 is in synchronization with the input signal (the photoplethysmographic signal). Note that a signal based on a result of the analysis performed by the biological signal analyzing unit 30 (the SN analyzing unit 31 and the PF analyzing unit 32) is outputted to the parameter control unit 40.

The parameter control unit 40 changes constants of the variable loop filter 22 by switching among a plurality of different modes in which the cutoff frequency and the phase margin of the variable loop filter 22 differ, based on the analysis result from the biological signal analyzing unit 30, or in other words, on the basis of the SN ratio estimated by the SN analyzing unit 31 and the phase difference/frequency difference between the photoplethysmographic signal and the oscillation signal analyzed by the PF analyzing unit 32.

To be more specific, the present embodiment is configured so that the stated plurality of modes includes a noise mode, a following mode, and a normal mode, and the constants of the variable loop filter 22 are switched using these three modes. In the case where it is determined that the SN ratio analyzed by the SN analyzing unit 31 is lower than a predetermined threshold value, the parameter control unit 40 determines that artifacts caused by body movement or the like are superimposed on the photoplethysmographic signal, and switches the constants of the variable loop filter 22 to the noise mode, in which the cutoff frequency is lower and the phase margin is greater than in the following mode. On the other hand, in the case where it is determined that the SN ratio calculated by the SN analyzing unit 31 is higher than the stated threshold value and the phase difference/frequency difference resulting from the analysis performed by the PF analyzing unit 32 are greater than a predetermined value despite it being determined that biological artifacts are not superimposed, the parameter control unit 40 determines that the PLL is not in synchronization with the photoplethysmographic signal in which artifacts are not superimposed, and switches the constants of the variable loop filter 22 to the following mode, in which the cutoff frequency is higher and the phase margin is lower.

Meanwhile, in the case where it is determined that the SN ratio calculated by the SN analyzing unit 31 is high and no biological artifacts are superimposed, and the result of the analysis performed by the PF analyzing unit 32 indicates that the phase difference/frequency difference is low, the parameter control unit 40 determines that the PLL is in synchronization with the photoplethysmographic signal in which artifacts are not superimposed, and switches the constants of the variable loop filter 22 to the normal mode, which is positioned between the following mode and the noise mode.

When switching among the stated three modes, the parameter control unit 40 controls the phase margin of the variable loop filter 22 by dynamically adjusting the phase range of the differential (D) element of the variable loop filter 22. In other words, the parameter control unit 40 determines the magnitude of the phase margin by dynamically adjusting the range of time constants T1 and T2 $((1/T1)<(1/T2))$ of a transfer function of the variable loop filter 22, as indicated in the following Formula (2).

Formula 2

$$F(s) = K \frac{(sT_1 + 1)}{s(sT_2 + 1)} \quad (2)$$

Here, FIG. 2 illustrates an example in which the transfer function indicated in Formula (2) is configured as an analog active filter. However, the transfer function of the variable loop filter 22 is not limited to the stated Formula (2), and it is sufficient for the numerator and denominator of the transfer function to be at least partially constituted by (sT1+1) and (sT2+1), respectively, and the condition of (1/T1)<(1/T2), as in the following Formula (3). Note that X(s) in Formula (3) may be any transfer function as long as the characteristics of the PLL unit 20 can be realized.

Formula 3

$$F(s) = K \frac{(sT_1 + 1)}{(sT_2 + 1)} X(s) \quad (3)$$

It is preferable that the threshold value used in the mode switch prevent erroneous operations (hunting) at the time of the switch by being provided with appropriate hysteresis characteristics.

Note that the method for realizing the variable loop filter 22 is not limited to the above-described analog circuit (filter), and may be realized through digital signal processing. In this case, the transfer function of the analog filter determined through the stated Formula (3) is converted to a digital filter transfer function through an s-z transform, and the variable loop filter 22 is configured as the IIR filter illustrated in FIG. 3. Here, the mode (constants) switched by the variable loop filter 22 in response to analysis result from the biological signal analyzing unit 30 is carried out by switching the tap coefficient of the IIR filter illustrated in FIG. 3 using software. However, noise will arise in the output signal of the IIR filter if the tap coefficient is simply switched, and thus it is preferable that the value of a delay device in the IIR filter be adjusted at the time of the switch.

In this manner, the constants of the variable loop filter 22 are dynamically controlled by the parameter control unit 40 on the basis of the analysis result from the SN analyzing unit 31 (the SN ratio) and the analysis result from the PF analyzing unit 32 (the phase difference/frequency difference), which constitute the biological signal analyzing unit 30.

The biological information obtainment unit 50 obtains biological information such as a pulse rate, a pulse beat interval, or the like on the basis of the output signal of the voltage controlled oscillation unit 23 (the oscillation signal). The biological information obtainment unit 50 may convert this information to an instant pulse rate on the basis of the output signal of the variable loop filter 22 and obtain that instant pulse rate as the biological information. Note that the obtained biological information such as a pulse rate is outputted to the exterior or stored in the aforementioned RAM or the like.

Figure 4:
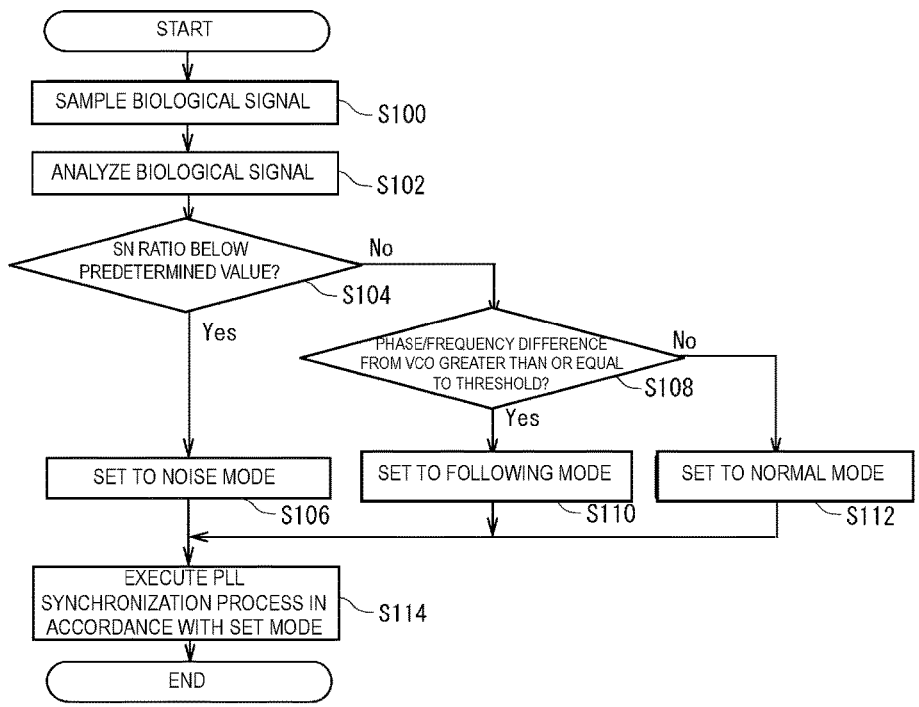
FIG. 4 is a flowchart illustrating the sequence of a biological information measurement process carried out by the biological information measurement apparatus according to the first embodiment.

Next, operations of the biological information measurement apparatus 1 will be described with reference to FIG. 4. FIG. 4 is a flowchart illustrating the sequence of a biological information measurement process carried out by the biological information measurement apparatus 1. The processes indicated in FIG. 4 are repeatedly executed at a predetermined timing, primarily by the signal processing unit 5.

In step S100, the biological signal (photoplethysmographic signal) is sampled. Next, in step S102, the photoplethysmographic signal sampled in step S100 is analyzed by the SN analyzing unit 31 and the PF analyzing unit 32. The details of the analysis performed by the SN analyzing unit 31 and the PF analyzing unit 32 are as described above and thus detailed descriptions thereof will be omitted here.

Next, in step S104, it is determined whether or not the analysis result from the SN analyzing unit 31 (the SN ratio) is less than a predetermined value. In the case where the SN ratio is less than the stated predetermined value (that is, in the case where there are many artifacts), the process moves to step S106. On the other hand, when the SN ratio is greater than or equal to the stated predetermined value (that is, when there are few artifacts), the process moves to step S108.

In step S106, it is determined that artifacts are superimposed, and the constants of the variable loop filter 22 are set to the noise mode (that is, a mode in which the output of the voltage controlled oscillation unit 23 will not change even if artifacts are superimposed, where the cutoff frequency is low and the phase margin is high). The process then moves to step S114.

On the other hand, when it is determined that artifacts are not superimposed, in step S108, it is determined, on the basis of the analysis result from the PF analyzing unit 32, whether or not the phase difference/frequency difference between the photoplethysmographic signal and the oscillation signal of the voltage controlled oscillation unit 23 is greater than or equal to a predetermined threshold value. The process moves to step S110 in the case where the phase difference/frequency difference is greater than or equal to the predetermined threshold value. On the other hand, the process moves to step S112 in the case where the phase difference/frequency difference is less than the predetermined threshold value.

In step S110, it is determined that the PLL is not in synchronization, and the constants of the variable loop filter 22 are set to the following mode (that is, a mode in which the input signal can be followed quickly, where the cutoff frequency is high and the phase margin is low). The process then moves to step S114.

On the other hand, in step S112, it is determined that a sufficient state of synchronization is achieved, and the constants of the variable loop filter 22 are set to the normal mode (that is, a mode providing values between the noise mode and the following mode). The process then moves to step S114.

In step S114, a PLL synchronization process is executed in accordance with the mode set in step S106, step S110, or step S112. The process then exits this sequence at a certain period of time. In this manner, the cutoff frequency and the phase margin of the variable loop filter 22 are changed by switching among the three modes. As a result, a high level of both robustness with respect to artifacts and a reduction in lock-up time can be achieved.

Next, a lock-up time reduction result and a result of improving robustness with respect to artifacts achieved through the mode switching in the biological information measurement apparatus 1 will be described in terms of simulation results, using FIGS. 5 and 6.

First, the lock-up time reduction result achieved through the mode switching in the biological information measurement apparatus 1 will be described with reference to FIG. 5. FIG. 5 is a graph illustrating a lock-up time reduction result achieved through mode switching in the biological information measurement apparatus 1. FIG. 5 illustrates the output signal of the variable loop filter 22 when a sine wave corresponding to 120 (bpm) is inputted into the PLL unit 20. The output signal is indicated as a bpm conversion value for the purposes of these descriptions. The horizontal axis in FIG. 5 represents time (sec), and the vertical axis represents the output (bpm) of the variable loop filter 22. In FIG. 5, the output (bpm conversion value) of the variable loop filter 22 during the normal mode is represented by a broken line, whereas the output (bpm conversion value) of the variable loop filter 22 in the case where the mode is switched from the following mode to the normal mode is represented by a solid line.

Figure 5:
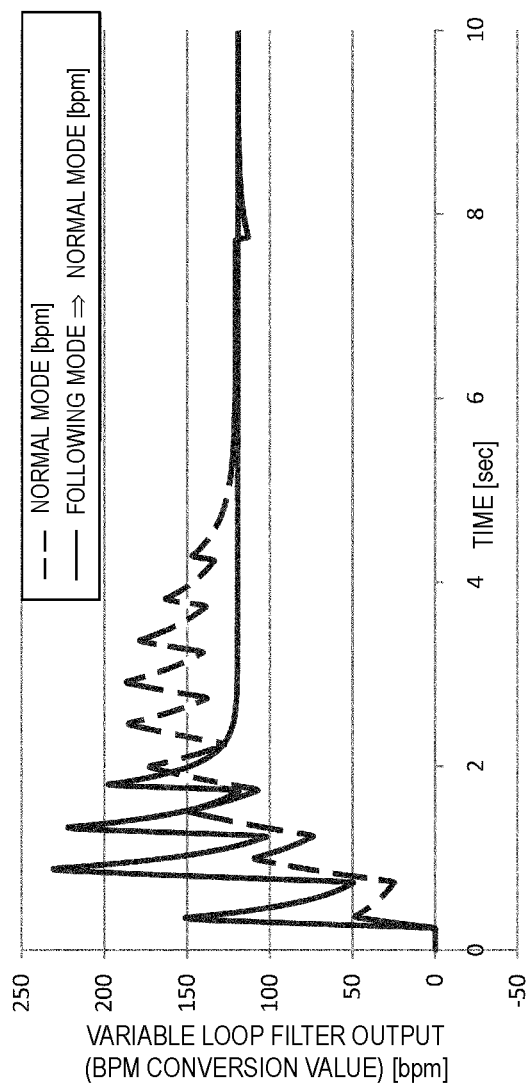
FIG. 5 is a graph illustrating a lock-up time reduction result achieved through mode switching in the biological information measurement apparatus according to the first embodiment.

As described above, in the case where a sine wave corresponding to 120 (bpm) is inputted into the PLL unit 20, it was confirmed that the lock-up time can be shortened more by dynamically switching from the following mode to the normal mode (the solid line) than through PLL synchronization operations in the normal mode only (the broken line), as illustrated in FIG. 5. Note that the switch from the following mode to the normal mode is carried out at approximately 2 seconds in the example illustrated in FIG. 5.

Next, a result of improving the robustness with respect to artifacts in the biological information measurement apparatus 1 will be described with reference to FIG. 6. Here, FIG. 6 is a graph illustrating a difference in the influence of artifacts in the biological information measurement apparatus 1 between the normal mode and the noise mode, or in other words, a result of improving the robustness with respect to artifacts. FIG. 6 illustrates the output signal of the variable loop filter 22 in the normal mode and in the noise mode, respectively, in the case where artifacts are superimposed on the biological signal and noise is superimposed on the input into the phase/frequency comparison unit 21. Like FIG. 5, the output signal is indicated as a bpm conversion value for the purposes of these descriptions. The horizontal axis in FIG. 6 represents time (sec), and the vertical axis represents the output (bpm) of the variable loop filter 22. In FIG. 6, the output (bpm conversion value) of the variable loop filter 22 during the normal mode is represented by a broken line, whereas the output (bpm conversion value) during the noise mode is represented by a solid line.

Figure 6:
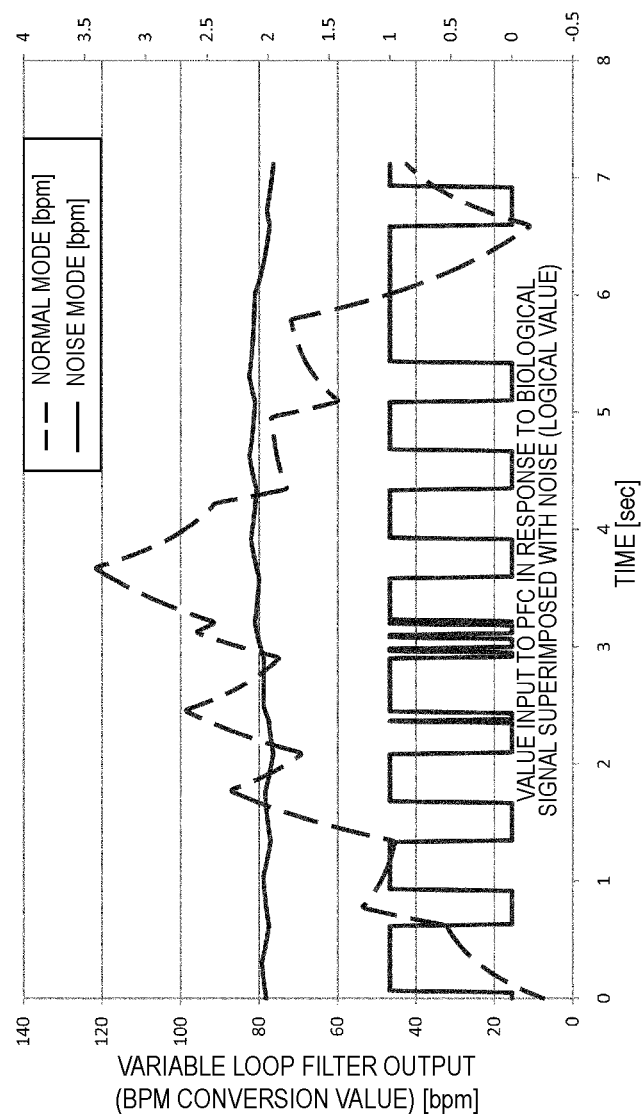
FIG. 6 is a graph illustrating a result of improving robustness with respect to artifacts in the biological information measurement apparatus according to the first embodiment.

As illustrated in FIG. 6, it was confirmed that the output of the variable loop filter 22 fluctuates less with respect to artifacts in the noise mode (the solid line) than in the normal mode (the broken line) in the case where artifacts are superimposed on the biological signal. From the stated results (those indicated in FIGS. 5 and 6), it was furthermore confirmed that the biological information measurement apparatus 1 can eliminate a tradeoff between a shortening of lock-up time and robustness with respect to artifacts by appropriately switching the mode (that is, the constants of the variable loop filter 22).

As described thus far, according to the present embodiment, the constants of the variable loop filter 22 are dynamically changed in response to the analysis result from the SN analyzing unit 31 (the SN ratio) and the analysis result from the PF analyzing unit 32 (the phase difference/frequency difference). As such, the PLL can be synchronized more appropriately in accordance with fluctuations in the frequency of the inputted photoplethysmographic signal (the pulse rate), the state of artifacts, and so on. As a result, an output signal that is not susceptible to the influence of artifacts can be obtained in the case where artifacts are superimposed on the photoplethysmographic signal, and the PLL lock-up time can be reduced in the case where no artifacts are superimposed. Accordingly, robustness with respect to artifacts and a reduction in lock-up time can both be achieved at an even higher level.

According to the present embodiment, the phase margin of the variable loop filter 22 is adjusted by dynamically changing the phase range of the differential element of the variable loop filter 22. Accordingly, by changing the phase range of the differential (D) element of the variable loop filter 22 to adjust the phase margin, the convergence properties of the variable loop filter 22 can be adjusted.

In particular, according to the present embodiment, a mode is switched among three modes (the noise mode, the following mode, and the normal mode), which have different cutoff frequencies and the phase margins, on the basis of the SN ratio estimated by the SN analyzing unit 31 and the phase difference/frequency difference analyzed by the PF analyzing unit 32. Accordingly, the cutoff frequency and the phase margin can be changed by switching among the three modes. As a result, an output signal that is not susceptible to the influence of artifacts can be obtained in the case where artifacts are superimposed on the photoplethysmographic signal, and the PLL lock-up time can be reduced in the case where no artifacts are superimposed. Accordingly, both robustness with respect to artifacts and a reduction in lock-up time can be achieved at a high level.

Furthermore, according to the present embodiment, the phase range of the differential (D) element of the variable loop filter 22 is adjusted when switching among the stated three modes. Accordingly, the magnitude of the phase margin of the variable loop filter 22 can be adjusted, and the convergence properties of the variable loop filter 22 can be changed, by switching the mode.

Furthermore, according to the present embodiment, the threshold value at which a switch is made among the three modes is provided with hysteresis, and thus erroneous operations (hunting) can be prevented from occurring when the mode is switched.

Second Embodiment

The biological information measurement apparatus 1 according to the above-described first embodiment is configured so that the biological signal analyzing unit 30 includes the SN analyzing unit 31 and the PF analyzing unit 32, and estimates the SN ratio of the photoplethysmographic signal by carrying out an autocorrelation analysis on the photoplethysmographic signal (the biological signal), and analyzes the phase difference/frequency difference between the photoplethysmographic signal and the oscillation signal with respect to the output of the phase/frequency comparison unit 21. However, the configuration may be such that the frequency analysis is carried out by executing an orthogonal transform such as an FFT on the photoplethysmographic signal and detecting a state of the photoplethysmographic signal, such as the approximate frequency, noise level, and the like of the photoplethysmographic signal, for example.

Accordingly, next, the configuration of a biological information measurement apparatus 2 according to a second embodiment will be described using FIG. 7. Here, descriptions of configurations that are identical or similar to those in the biological information measurement apparatus 1 according to the above-described first embodiment will be simplified or omitted, and primarily the points of difference will be described. FIG. 7 is a block diagram illustrating the configuration of the biological information measurement apparatus 2. In FIG. 7, constituent elements that are the same or equivalent to those in the first embodiment have been given the same reference numerals.

The biological information measurement apparatus 2 differs from the biological information measurement apparatus 1 in that a biological signal analyzing unit 30B is provided instead of the biological signal analyzing unit 30 that includes the SN analyzing unit 31 and the PF analyzing unit 32. The other configurations are the same or similar to those in the aforementioned biological information measurement apparatus 1, and thus detailed descriptions thereof will be omitted.

The biological signal analyzing unit 30B obtains an approximate frequency, phase, and SN ratio (a noise state) of an inputted photoplethysmographic signal by analyzing the photoplethysmographic signal. To be more specific, by carrying out an orthogonal transform such as an FFT on the photoplethysmographic signal, the biological signal analyzing unit 30B obtains the approximate frequency of the photoplethysmographic signal, determines a frequency component that differs from that frequency component (the frequency component of a photoplethysmograph being 0.666-6.666 Hz, for example) to be noise, and finds a level and the like of that noise.

It should be noted that according to the biological signal analyzing unit 30B, the state of the photoplethysmographic signal may be analyzed on the basis of one or more of the output signal of the phase/frequency comparison unit 21, the output signal of the variable loop filter 22, and the output signal of the voltage controlled oscillation unit 23, instead of or in addition to the inputted photoplethysmographic signal.

As in the above-described first embodiment, the parameter control unit 40 dynamically changes the constants of the variable loop filter 22 on the basis of the analysis results from the biological signal analyzing unit 30B, or in other words, on the basis of the approximate frequency, phase, and SN ratio (noise state) of the photoplethysmographic signal.

Note that the biological signal analyzing unit 30B may determine the state of the photoplethysmographic signal by carrying out a time-series analysis on the photoplethysmographic signal. In this case, the state of the photoplethysmographic signal is determined by carrying out a time-series analysis for detecting a seasonal component (pulse beat component) contained in the photoplethysmographic signal and a noise component caused by artifacts.

According to the present embodiment, the approximate frequency, phase, and SN ratio of the photoplethysmographic signal are analyzed, and the constants of the variable loop filter 22 are dynamically changed on the basis of the result of that analysis. As such, the appropriate phase/frequency synchronization can be achieved in accordance with fluctuations in the frequency of the inputted photoplethysmographic signal (the pulse rate), the state of artifacts, and so on. As a result, an output signal that is not susceptible to the influence of artifacts can be obtained in the case where artifacts are superimposed on the photoplethysmographic signal, and the PLL lock-up time can be reduced in the case where no artifacts are superimposed. Accordingly, robustness with respect to artifacts and a reduction in lock-up time can both be achieved at a high level.

In particular, according to the present embodiment, the frequency, SN ratio, and the like of the photoplethysmographic signal are analyzed by carrying out an orthogonal transform (FFT) on the photoplethysmographic signal. As such, the approximate frequency and SN ratio of the photoplethysmographic signal, in which the pulse rate varies over time and on which artifacts produced by body movements and the like are superimposed, can be analyzed appropriately.

Although embodiments of the present invention have been described thus far, the present invention is not intended to be limited to the aforementioned embodiments, and many variations can be carried out thereon. For example, although the above embodiments describe configurations in which biological information such as a pulse rate is measured by detecting a photoplethysmographic signal (a biological signal) using the photoplethysmographic sensor 10, the configuration may be such that biological information such as a pulse rate is measured by detecting an electrocardiac signal (biological signal) using an electrocardiac sensor, for example, instead of or in addition to the photoplethysmographic sensor 10.

The above embodiments describe configurations in which the constants of the variable loop filter 22 are changed by switching among three modes (the noise mode, the following mode, and the normal mode) having different cutoff frequencies and phase margins for the variable loop filter 22 on the basis of the analysis results from the biological signal analyzing unit 30, or in other words, on the basis of the SN ratio estimated by the SN analyzing unit 31 and the phase difference/frequency difference of the photoplethysmographic signal analyzed by the PF analyzing unit 32. However, the number of modes is not limited to three. Furthermore, the configuration may be such that the stated constants are changed consecutively instead of switching among modes.

REFERENCE SIGNS LIST 1, 2 BIOLOGICAL INFORMATION MEASUREMENT APPARATUS
5, 6 SIGNAL PROCESSING UNIT
10 PHOTOPLETHYSMOGRAPHIC SENSOR
20 PLL UNIT
21 PHASE/FREQUENCY COMPARISON UNIT
22 VARIABLE LOOP FILTER
23 VOLTAGE CONTROLLED OSCILLATION UNIT
30, 30B BIOLOGICAL SIGNAL ANALYZING UNIT
31 SN ANALYZING UNIT
32 PHASE/FREQUENCY ANALYZING UNIT
40 PARAMETER CONTROL UNIT
50 BIOLOGICAL INFORMATION OBTAINMENT UNIT

The invention claimed is:

1. A biological information measurement apparatus comprising:
   a sensor configured to detect a biological signal;
   a phase/frequency comparator configured to output a deviation signal based on a phase difference/frequency difference between the biological signal and an oscillation signal;
   a variable loop filter having at least one of a variable cutoff frequency and variable phase margin, the variable loop filter selectively blocking a signal of a predetermined frequency band contained in the deviation signal;
   a voltage controlled oscillator coupled to the phase/frequency comparator and configured to generate the oscillation signal based on the deviation signal that has been filtered by the variable loop filter; and
   a computer processing unit configured to analyze a phase, a frequency, and a SN ratio of the biological signal, and change at least one constant of the variable loop filter based on the analyzed phase, frequency and SN ratio of the biological signal to control at least one of the cutoff variable frequency and variable phase margin of the variable loop filter.

2. The biological information measurement apparatus according to claim 1, wherein the computer processing unit is configured to analyze the phase, the frequency, and the SN ratio of the biological signal by an orthogonal transformation of the biological signal.

3. The biological information measurement apparatus according to claim 1, wherein the computer processing unit is further configured to:
   estimate the SN ratio of the biological signal based on an autocorrelation of the biological signal,
   analyze the phase difference/frequency difference between the biological signal and the oscillation signal based on the deviation signal output by the phase/frequency comparator, and
   change the constants of the variable loop filter based on the estimated SN ratio and the analyzed phase difference/frequency difference between the biological signal and the oscillation signal.

4. The biological information measurement apparatus according to claim 3, wherein the computer processing unit is configured to adjust the phase margin of the variable loop filter by adjusting a phase range of a differential element of the variable loop filter.

5. The biological information measurement apparatus according to claim 3, wherein the computer processing unit is configured to switch among a plurality of modes having different cutoff frequencies and different phase margins based on the estimated SN ratio and the analyzed phase difference/frequency between the biological signal and the oscillation signal.

6. The biological information measurement apparatus according to claim 5, wherein, to switch among the plurality of modes, the computer processing unit controls the phase margin of the variable loop filter by adjusting a phase range of a differential element of the variable loop filter.

7. The biological information measurement apparatus according to claim 5, wherein a threshold value is provided with hysteresis by the computer processing unit to switch among the plurality of modes.

8. The biological information measurement apparatus according to claim 5,
   wherein the plurality of modes includes a noise mode, a following mode, and a normal mode, and
   the noise mode has the cutoff frequency that is lower and the phase margin that is higher than the following mode,
   the following mode has the cutoff frequency that is higher and the phase margin that is lower than in the noise mode, and
   the normal mode has both the cutoff frequency and the phase margin between the respective cutoff frequencies and phase margins in the noise mode and the following mode.

9. The biological information measurement apparatus according to claim 8, wherein the computer processing unit is configured to select the noise mode when the SN ratio is lower than a predetermined value, select the following mode when the SN ratio is higher than the predetermined value and the phase difference/frequency difference is higher than a predetermined threshold value, and select the normal mode when the SN ratio is higher than the predetermined value and the phase difference/frequency difference is lower than the predetermined threshold value.

10. The biological information measurement apparatus according to claim 1, wherein the variable loop filter comprises an analog filter including an operational amplifier with a variable differential element.

11. The biological information measurement apparatus according to claim 1, wherein the variable loop filter comprises a second-order infinite impulse response filter that includes a plurality of adders, a plurality of delay elements, and a plurality of multipliers.

12. The biological information measurement apparatus according to claim 11, wherein the computer processing unit is configured to change at least one constant of the variable loop filter by changing at least one filter coefficient of at least one of the plurality of multipliers.

13. The biological information measurement apparatus according to claim 1, wherein the sensor includes:
   a light-emitting element that emits light based on a pulse-form driving signal;
   a light-receiving element that outputs a detection signal based on an intensity of incident light that has been emitted from the light-emitting element and passed through a human body or reflected by the human body; and
   an amplifying unit that amplifies the detection signal as the biological signal.

14. A method for measuring biological information, the method comprising:
   detecting, by a sensor, a biological signal;
   generating a deviation signal by comparing a phase difference/frequency difference between the biological signal and an oscillation signal;
   selectively blocking, by a variable loop filter having at least one of a variable cutoff frequency and variable phase margin, a signal of a predetermined frequency band contained in the deviation signal;
   generating, by a voltage controlled oscillator, the oscillation signal based on the deviation signal that has been filtered by the variable loop filter;
   analyzing, by a computer processing unit, a phase, a frequency, and a SN ratio of the biological signal; and
   changing, by a computer processing unit, at least one constant of the variable loop filter based on the analyzed phase, frequency and SN ratio of the biological signal to control at least one of the cutoff variable frequency and variable phase margin of the variable loop filter.

15. The method according to claim 14, further comprising analyzing, by the computer processing unit, the phase, the frequency, and the SN ratio of the biological signal by an orthogonal transformation of the biological signal.

16. The method according to claim 14, further comprising:
   estimating, by the computer processing unit, the SN ratio of the biological signal based on an autocorrelation of the biological signal;
   analyzing, by the computer processing unit, the phase difference/frequency difference between the biological signal and the oscillation signal based on the deviation signal; and
   changing, by the computer processing unit, the constants of the variable loop filter based on the estimated SN ratio and the analyzed phase difference/frequency difference between the biological signal and the oscillation signal.

17. The method according to claim 16, further comprising adjusting, by the computer processing unit, the phase margin of the variable loop filter by adjusting a phase range of a differential element of the variable loop filter.

18. The method according to claim 16, further comprising switching, by the computer processing unit, among a plurality of modes having different cutoff frequencies and different phase margins based on the estimated SN ratio and the analyzed phase difference/frequency between the biological signal and the oscillation signal.

19. The method according to claim 18,
   wherein the plurality of modes includes a noise mode, a following mode, and a normal mode, and
   the noise mode has the cutoff frequency that is lower and the phase margin that is higher than the following mode,
   the following mode has the cutoff frequency that is higher and the phase margin that is lower than in the noise mode, and
   the normal mode has both the cutoff frequency and the phase margin between the respective cutoff frequencies and phase margins in the noise mode and the following mode.

20. The method according to claim 19, further comprising:
   selecting, by the computer processing unit, the noise mode when the SN ratio is lower than a predetermined value;
   selecting, by the computer processing unit, the following mode when the SN ratio is higher than the predetermined value and the phase difference/frequency difference is higher than a predetermined threshold value; and
   selecting, by the computer processing unit, the normal mode when the SN ratio is higher than the predetermined value and the phase difference/frequency difference is lower than the predetermined threshold value.

* * * * *